(12) United States Patent
Zumbrunn et al.

(10) Patent No.: US 12,343,087 B2
(45) Date of Patent: Jul. 1, 2025

(54) PATIENT SPECIFIC FRACTURE PLATES WITH BONE FRAGMENT BASED SCREW ORIENTATION

(71) Applicants: ETH Zürich, Zürich (CH); The Brigham and Women's Hospital, Inc., Boston, MA (US)

(72) Inventors: Thomas Zumbrunn, Hasliberg (CH); Arvind Gabriel Von Keudell, Brookline, MA (US); Stephan J. Ferguson, Hinwil (CH)

(73) Assignees: ETH Zürich, Zürich (CH); The Brigham andWomen's Hospital, Inc., Boston, MA (US)

( * ) Notice: Subject to any disclaimer, the term of this patent is extended or adjusted under 35 U.S.C. 154(b) by 109 days.

(21) Appl. No.: 18/008,784

(22) PCT Filed: Jun. 2, 2021

(86) PCT No.: PCT/IB2021/054820
§ 371 (c)(1),
(2) Date: Dec. 7, 2022

(87) PCT Pub. No.: WO2021/250508
PCT Pub. Date: Dec. 16, 2021

(65) Prior Publication Data
US 2023/0218344 A1    Jul. 13, 2023

Related U.S. Application Data

(60) Provisional application No. 63/036,192, filed on Jun. 8, 2020.

(51) Int. Cl.
*A61B 34/10* (2016.01)
*A61B 17/56* (2006.01)
(Continued)

(52) U.S. Cl.
CPC .............. *A61B 34/10* (2016.02); *A61B 17/80* (2013.01); *A61B 2017/00526* (2013.01);
(Continued)

(58) Field of Classification Search
CPC .... A61B 2017/00526; A61B 2017/568; A61B 2034/102; A61B 2034/108; A61B 34/10;
(Continued)

(56) References Cited

U.S. PATENT DOCUMENTS 9,532,825 B2    1/2017   Geebelen
10,449,003 B2   10/2019  Reid et al.
(Continued)

FOREIGN PATENT DOCUMENTS

WO    WO-2018/170162 A1    9/2018

OTHER PUBLICATIONS

International Search Report & Written Opinion for PCT/IB2021/054820, dated Aug. 25, 2021, 16 pages.
(Continued)

*Primary Examiner* — Samuel S Hanna
(74) *Attorney, Agent, or Firm* — Blank Rome LLP

(57) ABSTRACT

The present invention provides a method for generating a bone fixation implant and related preoperative planning. The method comprises a first step of determining at least the orientation and the position of the fixation means, based on a 3D model of the bone fragments. The method may include a second step of defining the shape of one or more bone plates, based on the output of the first step. The method may further include a third step determining tools for applying fixation means during surgery, according the optimized configuration defined in the first step and applying the bone plates from the second step. The method may even further
(Continued)

Figure 1:
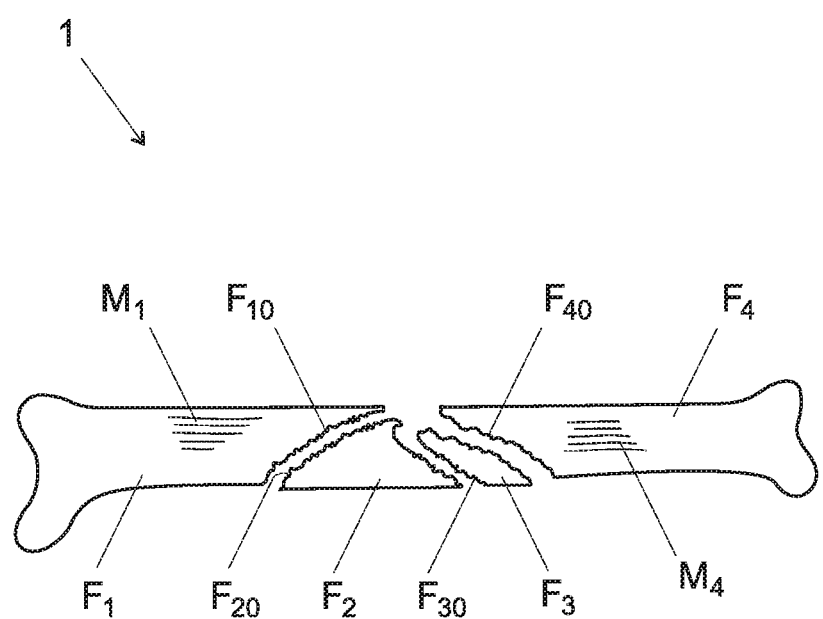

include a fourth step, quantifying construct stability for a given patient following surgery, thereby allowing early weightbearing.

16 Claims, 9 Drawing Sheets

(51) Int. Cl.
 *A61B 17/80* (2006.01)
 *A61B 17/00* (2006.01)
(52) U.S. Cl.
 CPC ... *A61B 2017/568* (2013.01); *A61B 2034/104* (2016.02); *A61B 2034/105* (2016.02); *A61B 2034/108* (2016.02)
(58) Field of Classification Search
 CPC ........ A61B 2034/105; A61B 2034/104; A61B 17/8061; A61B 17/6425; A61B 17/56; A61B 17/1728; A61B 17/80
 See application file for complete search history.

(56) References Cited

U.S. PATENT DOCUMENTS

| | | |
|---|---|---|
| 2018/0168731 A1* | 6/2018 | Reid ..................... A61B 34/10 |
| 2018/0235705 A1 | 8/2018 | Brown et al. |
| 2018/0271569 A1 | 9/2018 | Verstreken et al. |

OTHER PUBLICATIONS

R. V. O'Toole, III, et al., "Biomechanics for Preoperative Planning and Surgical Simulations in Orthopaedics", Comput. Biol . . . Med., Elsevier Science Ltd, 1995; vol. 25, No. 2, pp. 183-191.

M. Steiner, et al., "Numerical Simulation of Callus Healing for Optimization of Fracture Fixation Stiffness", PLOS ONE, www/plosone.org; Jul. 2014; vol. 9, Issue 7, 12 pgs.

Yong-Gon Koh, et al., "Multi-Objective Design Optimization of High Tibial Osteotomy for Improvement of Biomechanical Effect by Using Finite Element Analysis", Journal of Orthopaedic Research, Nov. 2018, 10 pgs.

* cited by examiner

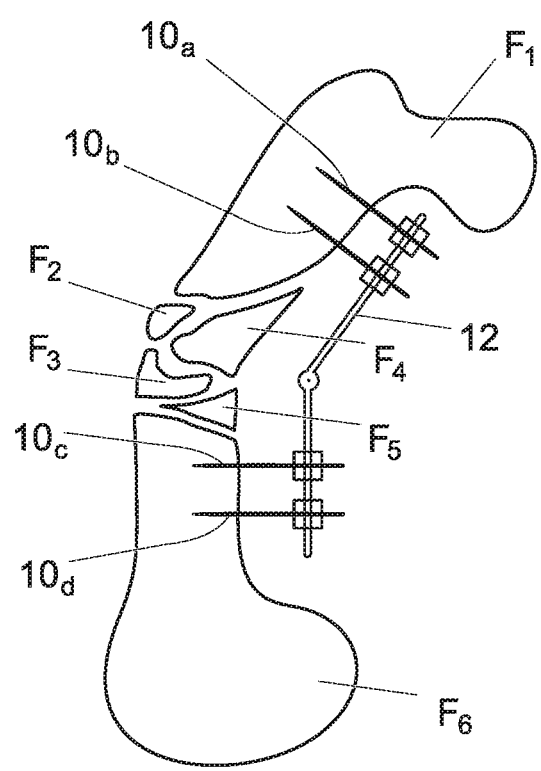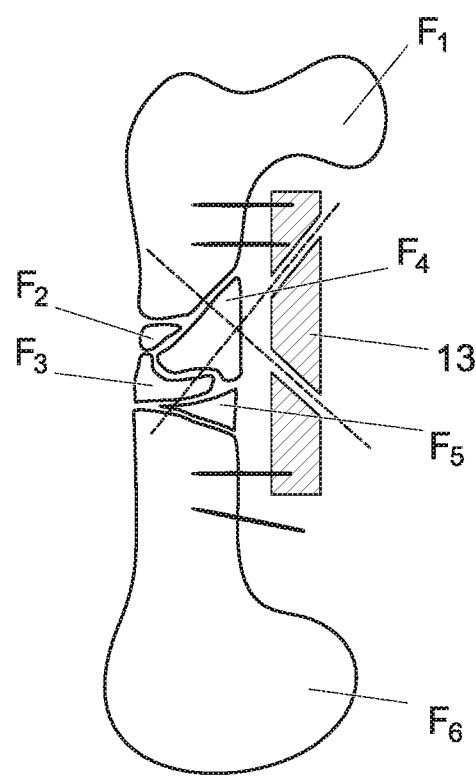
Fig. 10a  Fig. 10b
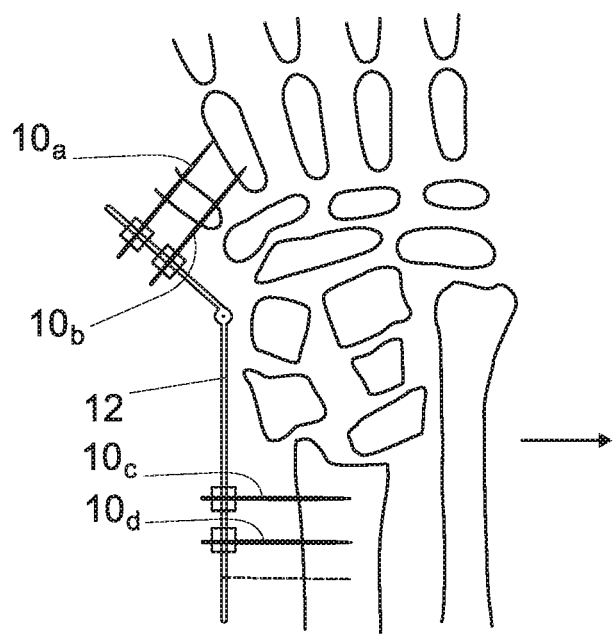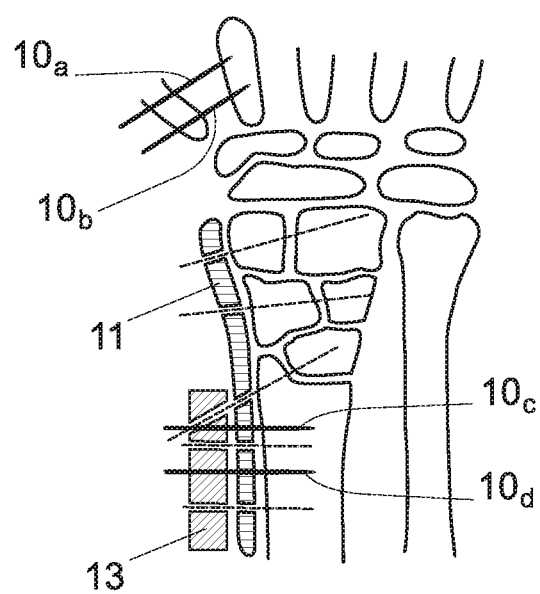
Fig. 10c  Fig. 10d

PATIENT SPECIFIC FRACTURE PLATES WITH BONE FRAGMENT BASED SCREW ORIENTATION

RELATED APPLICATIONS

This application is a national phase application of PCT/IB2021/054820, filed on Jun. 2, 2021, and claims priority to U.S. Provisional Application No. 63/036,192, filed on Jun. 8, 2020. The entire contents of these applications are hereby incorporated by reference in their entirety.

TECHNICAL DOMAIN

The present invention concerns a method for performing bone fracture surgery and interventions.

RELATED ART

Complex bone fractures, in particular related to articulations (periarticular fracture), need personalized solutions to limit or avoid complications, improve bone healing and/or reduce patient pain. Even though modern precontoured anatomic specific implants and particularly the development of locking screws have improved the capability of implants to fix and secure fractures with less extensive exposures, there is still a large portion of intraoperative trial and error involved to find a good fixation construct for adequate stability. Hence, complications are a common occurrence and failed fracture fixations are a common reason for referrals to specialists. Furthermore, such adverse events are often associated with deep infections and impaired bone healing, causing significant acceleration of the progression to posttraumatic arthritis. Depending on the involved joint, revision and reoperation-rates can reach up to 30%, which is unsatisfactorily high and associated with substantial personal and economic burdens.

Advanced planning software provide virtual 3D models and fragment alignment possibilities. In some cases, even standard implants and screws can be placed on the virtual bone model. Even though this allows for personalized planning, this process is still restricted by standard implant specifications and optimal fixation strategies may not be feasible with available implants. Further, surgical planning using these tools are subjective and solely relies on surgeons' judgment and experience (e.g. no quantitative measures).

The patent application US 20180271569 describes a method for generating bone plates according to patient-specific anatomical features so that the bone plate is better adapted to the bone surface than standard bone plates. Such bone plates may be produced based on 3D imaging of the treated bone and the desired final result. The U.S. Pat. No. 9,532,825 describes a similar approach for the production of guiding instruments involving the positioning of bone plates. The U.S. Pat. No. 10,449,003 describes a preoperative planning based on imaging results of the fractured bone, aiming at generating a large number of possible fixation designs. These documents merely rely on geometrical parameters without considering the daily life or non-medical parameters of the patients. Also, the methods described therein are based on qualitative evaluations, which may be subjected to approximations or lack of accuracy. In consequence, some operations do not lead to an optimal result. Some of patient should even be operated a second time to correct some deficiencies.

Short Disclosure of the Invention

An aim of the present invention is the provision of a improved method for producing a patient specific implant and personalized preoperative planning that overcomes the shortcomings and limitations of the state of the art. In particular, it is an object of the present invention to provide a method for producing a preoperative planning that avoids or limits the risk of reoperating patients. The present method of generating a preoperative planning aims at improving the rate of success, and the quality of the operations related to bone fractures, in particular to complex bone fractures.

Another aim of the invention is a preoperative planning tool usable by a surgeon to prepare the fixation of a fractured bone, in particular a complex fracture (e.g. periarticular), before the initiation of the fixation. It is in particular an aim of the present preoperative tool to allow the surgeon to quantify the fixation strength of a fractured bone. It is thus an objective of the preoperative planning tool to avoid or limit the subjective evaluations of the surgeon.

Another aim of the present invention is to provide a kit comprising at least one of a preoperative planning, an intra-operative assistance element, one or more of bone plate, and one or more instruments, including any guides and tools necessary for the implementation of the operation by a surgeon. Elements of the kit are provided so as to be consistent to a preoperative planning elaborated and/or validated by the above-mentioned method.

The above-mentioned objectives are realized by means of the method for generating a preoperative planning, the preoperative planning and the kit, object of the independent claims and further detailed in the dependent claims. It is here highlighted that a method for generating a preoperative planning is distinct from any method of treatment. The present method for generating a preoperative planning and the corresponding preoperative planning are based on quantitative parameters, thus avoiding or limiting any subjective evaluations or approximations of the surgeon. The present improved method of generating a preoperative planning and the corresponding preoperative planning is based not only on geometrical aspects of the bone fractures but also consider personal parameters of the patients, including health general status and daily activity. The method of generating a preoperative planning is computer implemented and based, or exclusively based, on real data and physical measurements.

SHORT DESCRIPTION OF THE DRAWINGS

Exemplar embodiments of the invention are disclosed in the description and illustrated by the following drawings:

FIG. 1 Schematic view of a fractured bone

Figure 2:
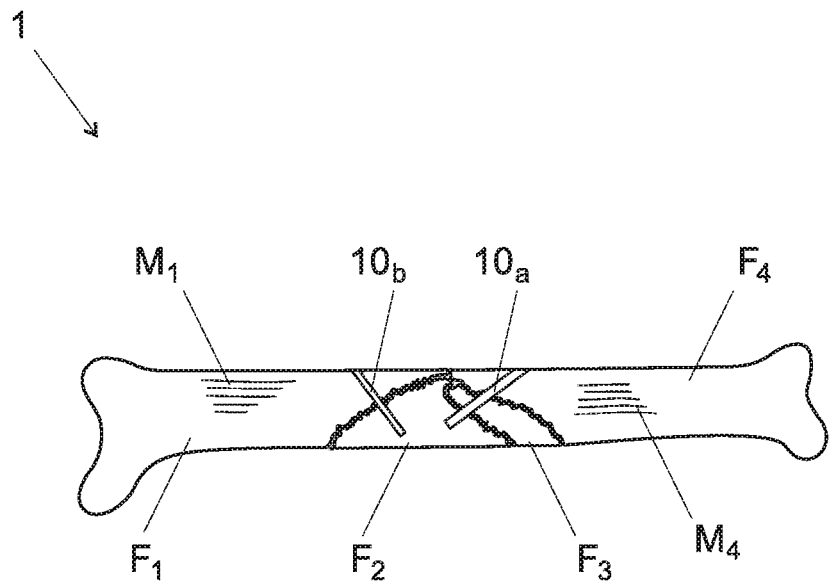
Figure 3:
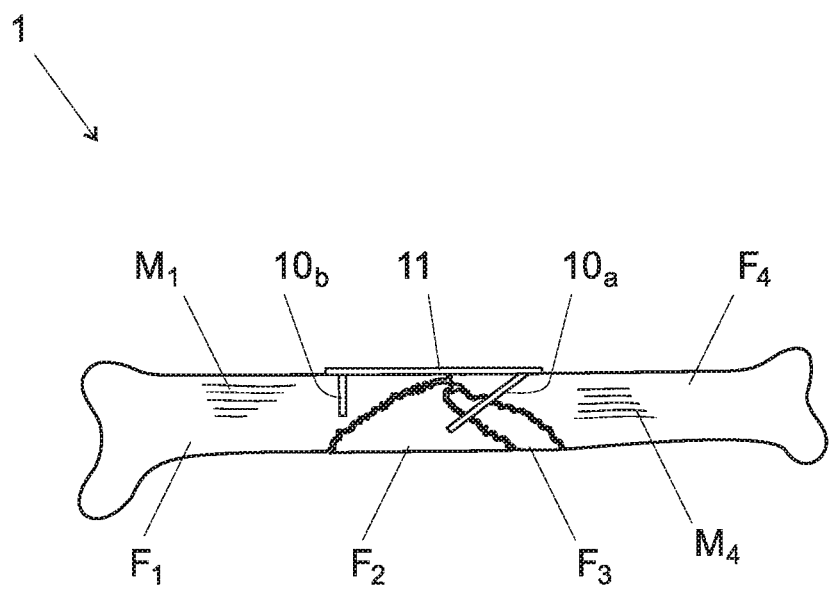

FIG. 2 Schematic view of an arrangement comprising the bone fragments and the fixation means FIG. 3 Schematic view of an arrangement comprising the bone fragments, the fixation means and a bone plate.

Figure 4:
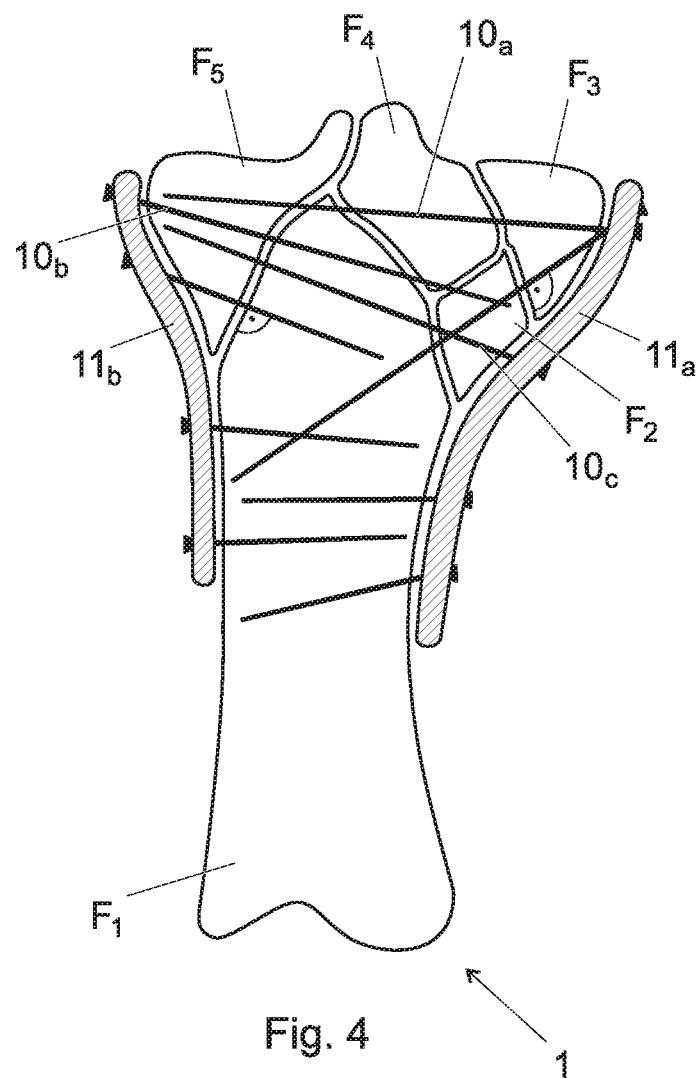

FIG. 4 Schematic longitudinal view of an arrangement comprising an articulation bone, fragments thereof, tailored bone plates and several fixation means, optimized for stability of each bone fragment and stiffness of the overall arrangement.

Figure 5:
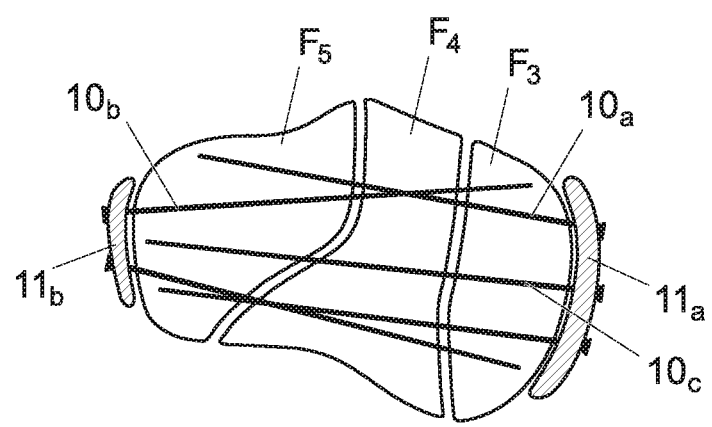

FIG. 5 Schematic top view of the arrangement of FIG. 4.

Figure 6A:
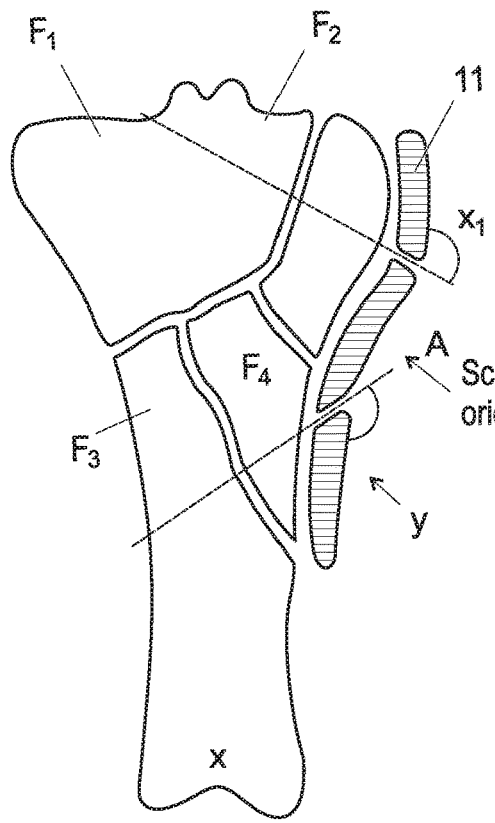
Figure 6B:
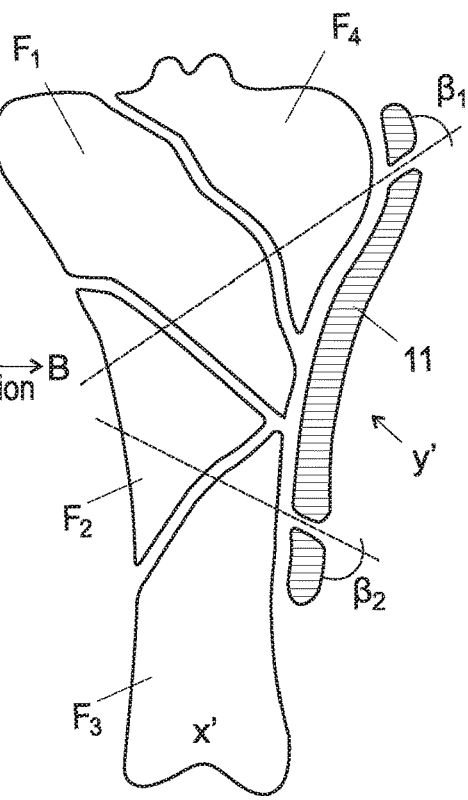
Figure 6C:
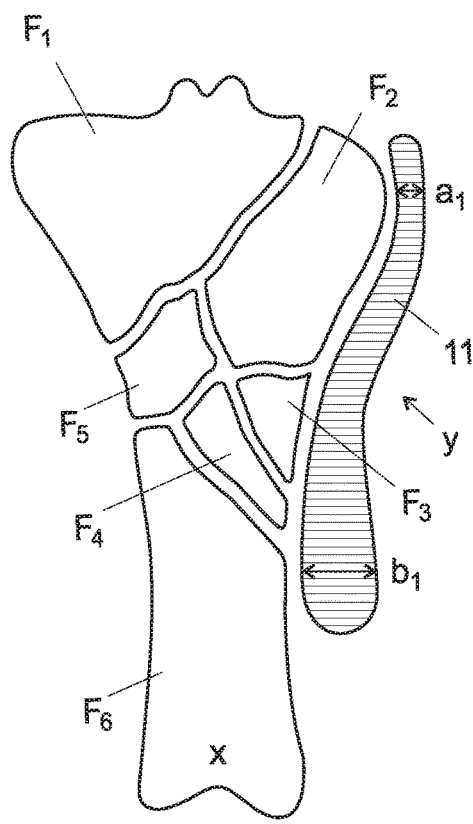
Figure 6D:
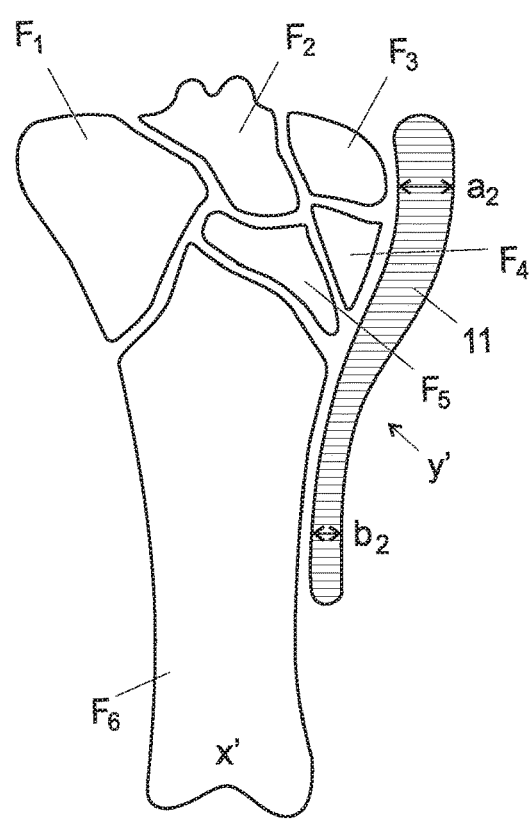

FIGS. 6a, 6b, 6c, 6d examples of varying implant parameters optimized for specific bone reconstructs, promoting improved healing based on the orientation of the fixation means or location dependent implant thickness (view of implant cross-section). FIGS. 6a and 6b show two similar implant designs with completely different orientation of the fixation means. FIGS. 6c and 6d show similar implant contour with location dependent thickness variation (e.g. varying cross-section for locally optimized implant stiffness).

Figure 7:
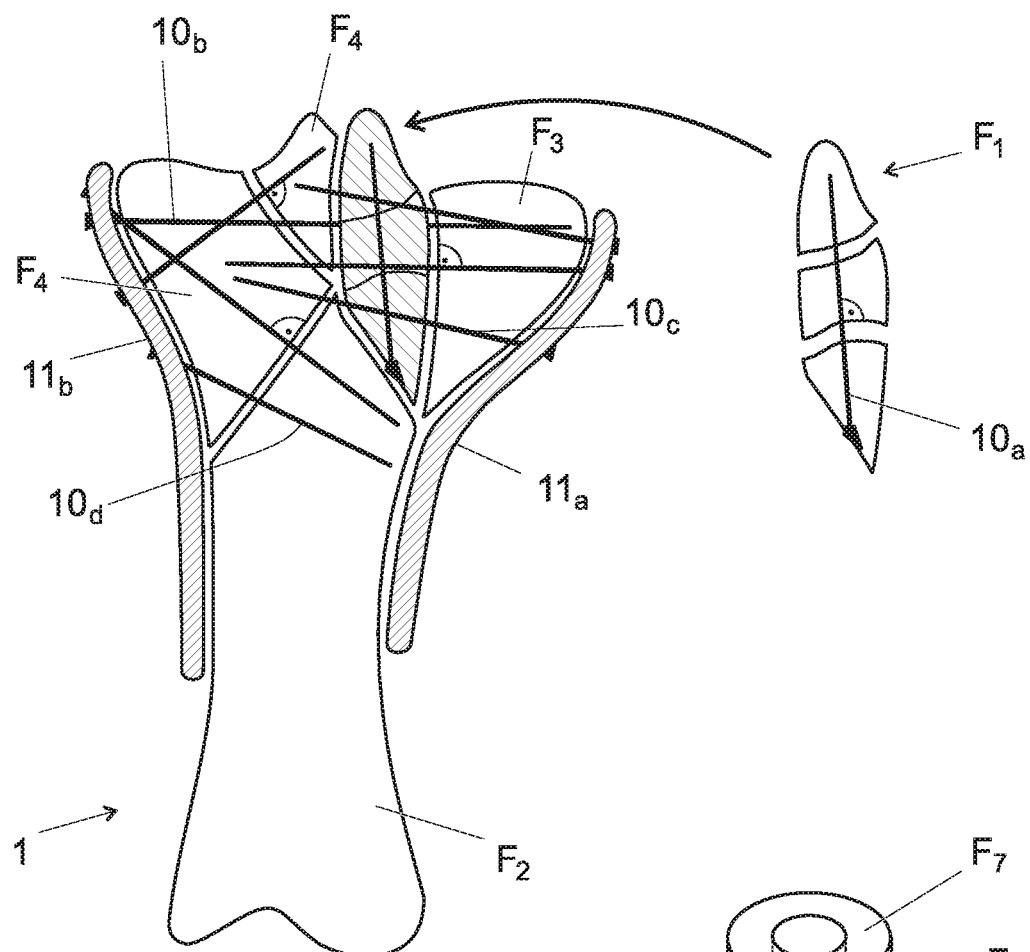

FIG. 7 Schematic example of a pre-construct element having independent fixation means (e.g. not directly accessible within overall bone construct), included in the bone reconstruction.

Figure 8:
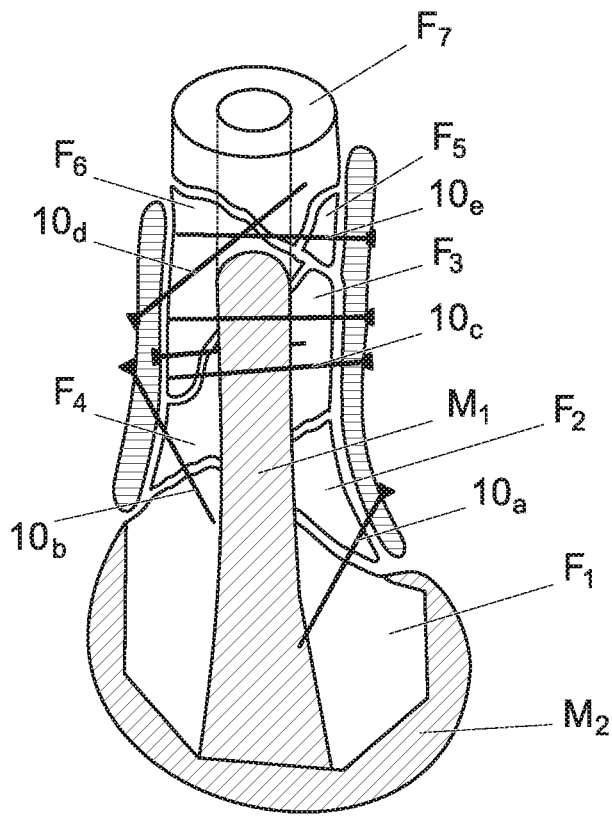

FIG. 8 Schematic example of an arrangement in the presence of pre-existing none-bone elements. This figure illustrates planning of bone plate design and fixation means around the pre-existing none-bone elements.

Figure 9:
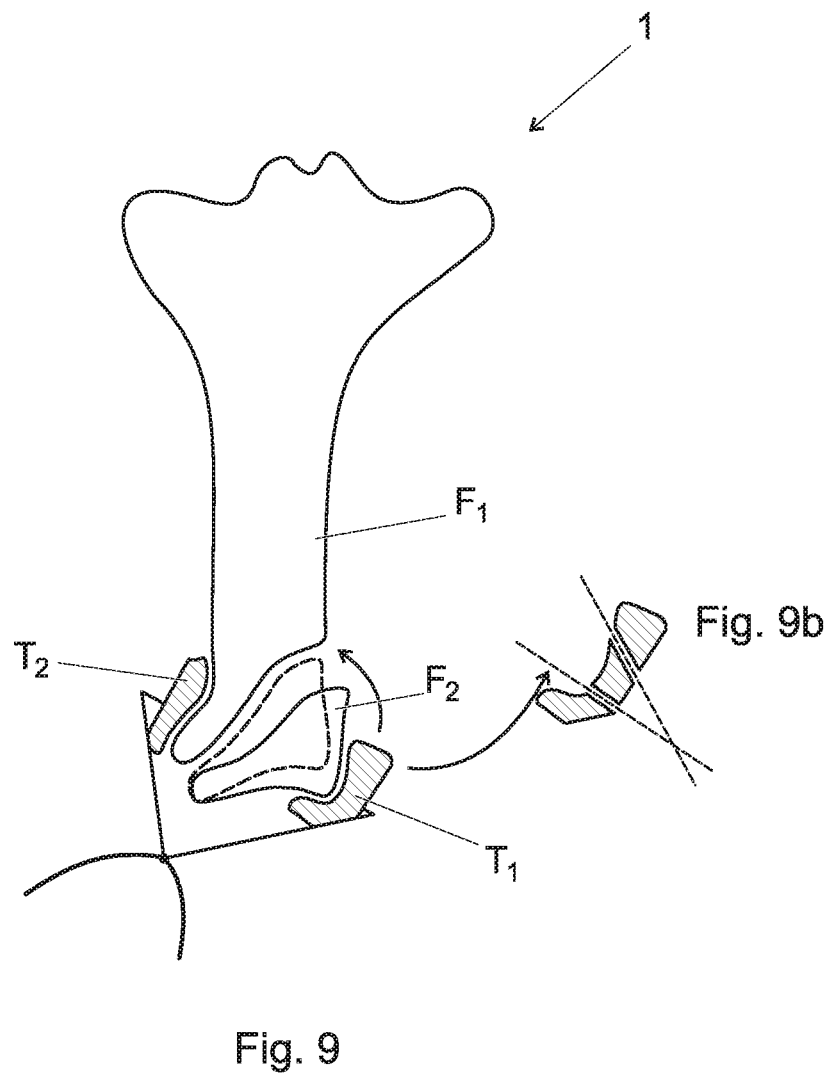

FIG. 9, 9b Schematic view of bone fragments in combination with an adapted instrument (e.g. personalized instrument-bone interface) temporarily maintaining said bone fragments. FIG. 9b shows the personalized instrument-bone interface that also allows fragment specific drilling for any temporary or permanent fixation means (i.e. the drilling can be performed while the adapted instrument holds fragments in the correct relative position).

FIGS. 10a, 10b schematic view of a femur fragments with temporary external fixation (10a) and femur fragments after reconstruction and final fixation including a drill guide with planned screw orientation.

FIGS. 10c, 10d: Schematic view of a hand with temporary external fixation (10c) and a hand after reconstruction with a bone plate a positioning guide and the corresponding pins.

Figure 11:
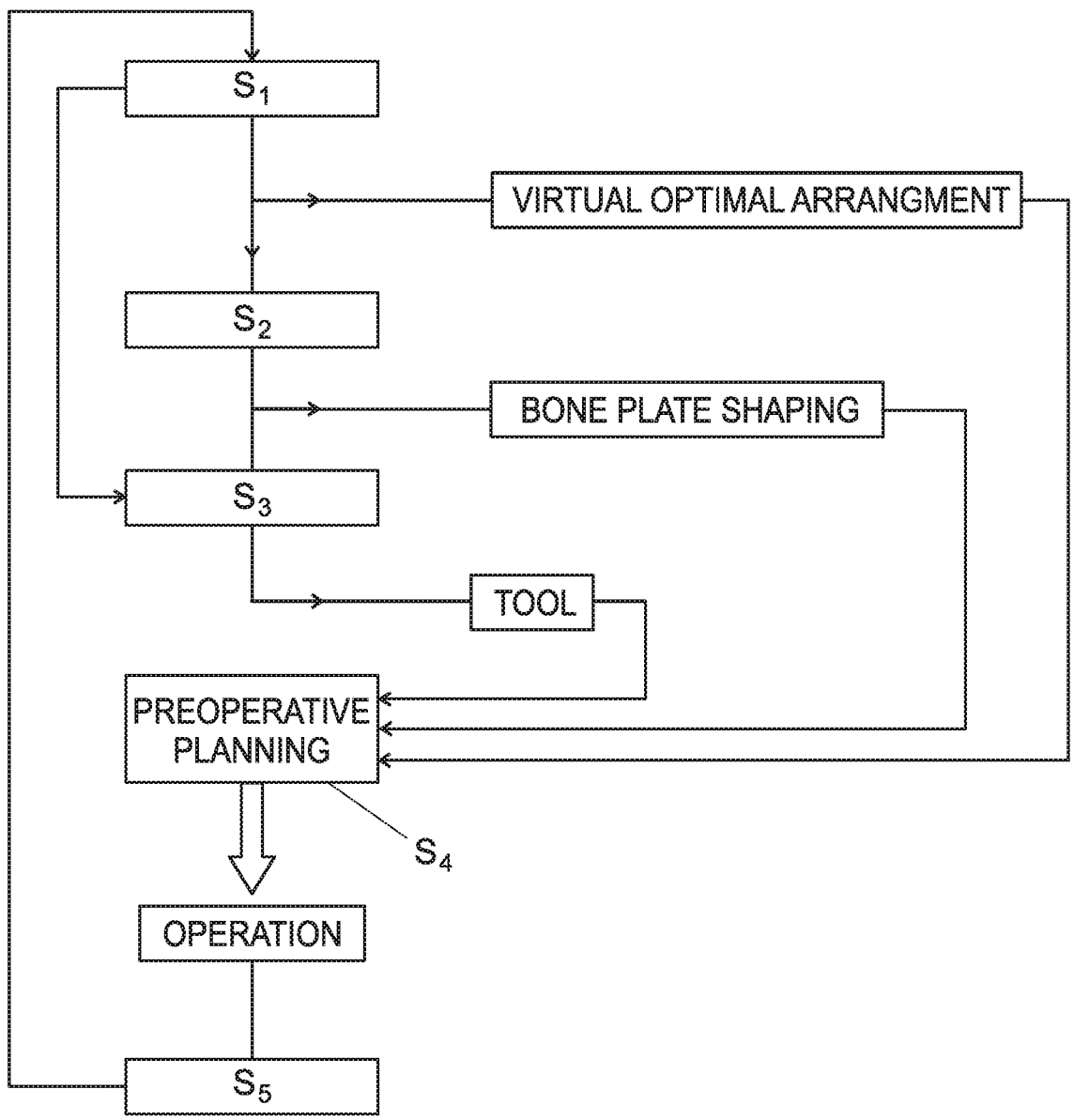
Figure 12:
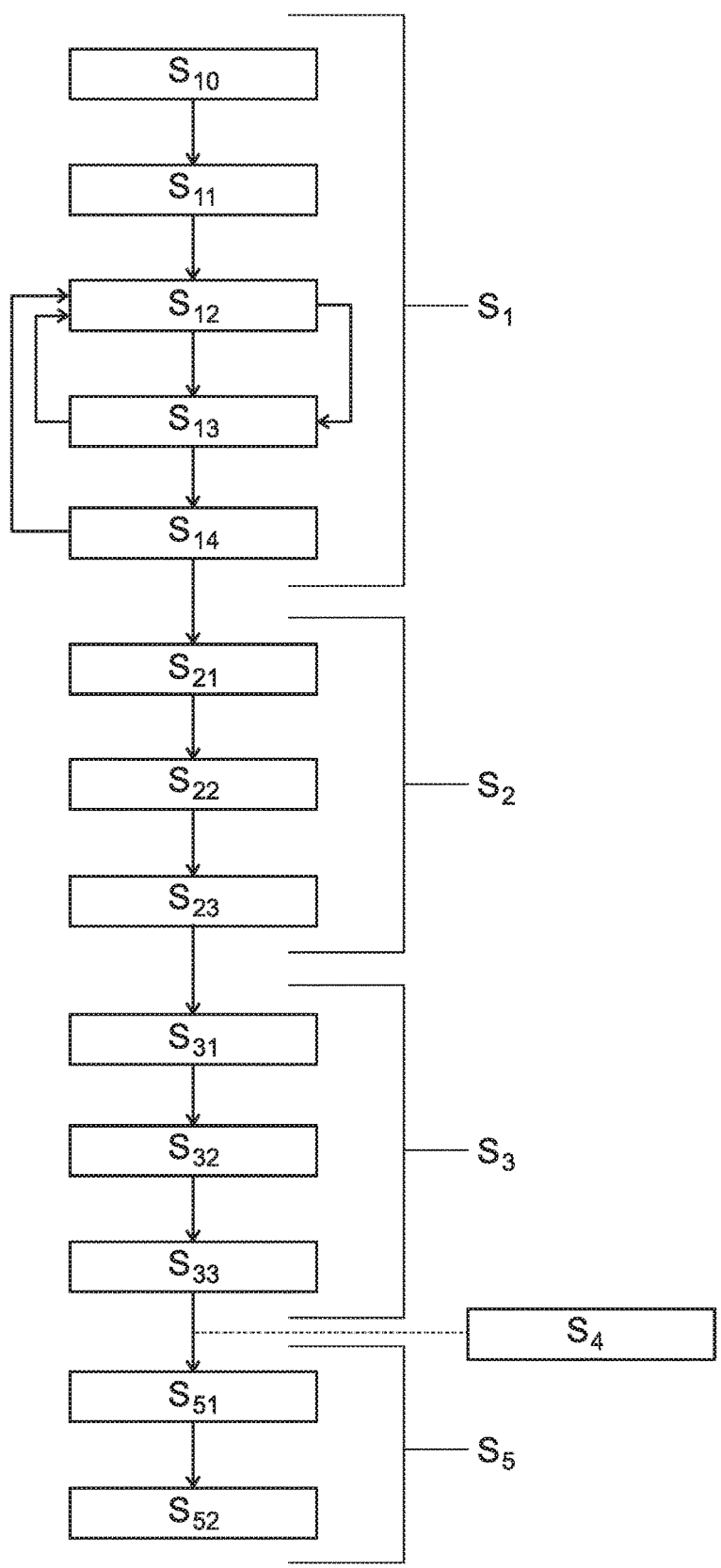

FIG. 11 Diagram referring to the main steps of the method according to the present invention FIG. 12 Diagram referring to the detailed steps of the method according to the present invention

EXAMPLES OF EMBODIMENTS OF THE PRESENT INVENTION

The FIG. 1 shows an example of a fractured bone 1, comprising several individual bone fragments F1, F2, F3, F4 and some specific areas M1, M2. The method of the present invention comprises a first step S1 aiming at determining one or more of the nature, the size, the number, the orientation and the position of the fixation means 10a, 10b, (FIG. 2) necessary to repair such a fractured bone 1. Based on medical imaging results, each one of the bone fragments F1, F2, F3, F4, is modelled. In particular, the individual modelling of the fragments F1, F2, F3, F4 allows to determine the 3D shape of the respective surfaces F10, F20, F30, F40. Such surfaces of the individual bone fragments include each of their surface resulting from the fracture, normally internal to the fractured bone 1, as well as the external surfaces.

The first step S1 thus comprises a 3D modelling step designated as a segmentation step S10 allowing to visualize the surfaces F10, F20, F30, F40 of the bone fragments F1, F2, F3, F4 and determine their complementarity. The 3D modelling step S10 also allows to visualize any element already present into the bone fragments or connected to them or surrounding them, such as bone implants, fixations pins, temporarily fixation means (e.g. external fixator).

Based on the geometry of the surfaces of the fragments F1, F2, F3, F4 of the fractured bone 1, the relative position of the bone fragments is precisely determined in a positioning step S11. The positioning step S11 may allow to define the original position of the bone fragments in the native bone before it fractured. Other positioning parameters may however be considered. For example, the bone fragments may be positioned relatively to one another in a way that allows the strongest arrangement or the most favourable healing process. The relative position of the bone fragments F1, F2, F3, F4 may be determined based on a degree of complementarity of their surfaces F10, F20, F30, F40, including the external surfaces. Iterative steps based on the relative position of the bone fragments may be computed in a way that a maximum level of complementarity is determined. Such a maximal complementarity can be considered as corresponding to the correct position of the bone fragments F1, F2, F3, F4. The correct position of the bone fragments is for example the relative position of the bone fragments which corresponds to their native position, before the fracture, or which is as close as possible of such a native position. Additional parameters may be considered in addition to the shape of the surfaces F10, F20, F30, F40 of the bone fragments, such as the interface gap between two contiguous bone fragments. The 3D imaging of each of the bone fragments F1, F2, F3, F4 may be obtained by any medical imaging technologies such as magnetic resonance imaging (MRI) scans, computer tomography (CT) scans, ultrasound, x-ray, etc. It is here understood that data related to the 3D imaging are digital or digitalized, so as to be computed according to the present method. Where applicable, the positioning step S11 may consider any external element already present and visualized during the previous step S10. Such external elements may be a previous implant for example.

Specific parameters such as the outer surface of the bone, also designated as the cortex, or more specifically a fractured articular surface (e.g. joint/periarticular fracture), which is interacting with the articular surface of another bone, either fractured or non-fractured, may be considered with superior importance for an optimized positioning. Reconstruction of periarticular fracture may be prioritized during the positioning step S11 to ensure proper joint function, following bone healing. This optimization may be based on the native anatomy or iterated through the following optimization steps, considering optimal joint loading. Further, the overall optimized positioning of each bone fragment may be based on an intact bone model, such as a mirrored bone from the contralateral side of the affected patient or from a database, matching size, shape, etc. or from a virtually computed desired model. Such virtually computed desired model includes artificial intelligence. For example, a deep learning algorithm may aid in finding this virtually desired model of aligned fracture fragments, based on an original anatomical geometry. Again, the articular surface, or other important areas may be prioritized, considering the optimal joint reconstruction over the rest of the bone. The positioning step S11 is thus understood as a reduction and/or reconstruction step. In particular, the positioning step aims at limiting or optimizing the gap between the bone fragments F1, F2, F3. A too large gap may have a negative impact on the healing process. All the bone fragments should be preferably in close contact to each other along their common surfaces F10, F20, F30, F40. It may however happen that some free space remains between two or more bone fragments. The positioning step thus allows to minimize this free space. Based on the 3D modelling step S10, the global free space may be determined and optimized. Alternatively or in addition, the average free space between two contiguous bone fragments may be determined and optimized. Thus either the average free space or the global free space can be optimized, or reduced, or minimized. If there is a large gap present, an optional step ("S111") can be performed, designing a gap geometry that can be used to fill the gap. This gap filling geometry can consist of various materials including bone grafts (patient's own bone or other bone material), polymer material a metal lattice material, resorbable magnesium material, etc. This geometry can be additively manufactured as part of the implant production step (S23) or form (negative geometry) can be generated in the instrument production step (S33) for intraoperative shaping or filling with bone material or bone cement etc. Alternatively, a 3D model can be produced for visualization of such gap and used as a reference geometry when generating a filling object (e.g. bone piece) during surgery. Thus, one or several different quantitative parameters such as contact surfaces, average gap, local gaps, volume of the free space between the bone fragments etc and any combination thereof, can be used to generate an optimized 3D arrangement of the bone fragments.

Besides the relative positioning of the bone fragments F1, F2, F3, F4, a stress level is determined for each of the bone fragments in a stress determination step S12. This stress determination step may be based on biomechanical simulations, including musculoskeletal modelling, finite element analysis (FEA), or other biomechanical testing, either virtual or physical. The stress determination step S12 may include various parameters such as von Mises Stress, principal stress, strain, deformation, displacement, reaction forces, etc. These biomechanical simulations may be completely personalized. To this end, elements comprising all bone fragments, muscle attachments to each specific fragment with magnitude and/or direction of forces, patients weight, patients activity, and all necessary element may be considered and specifically computerized. Alternatively, the biomechanical simulations may be semi-personalized wherein patient weight, relevant bone fragments and approximated fracture lines are considered. Still alternatively, the biomechanical simulations may be generalized, using limited patient information. In such a generalized model, the patient information may be limited to non-specific data such as estimated loads, a fracture type, and any other available non-specific data. The stress level determined in the stress determination step S12 includes the mechanical load applied to each of the bone fragments. In addition or alternatively, it includes the mechanical load applied to the whole construct of various bone fragments together. It can also include strain, displacement and other mechanical properties. The simulations and optimization may also include prioritized areas such as articular surfaces considering motion and load interaction with other bones through joints. The simulations can for example consider. minimizing motion between articular fragments. The stress determination step is based on biomechanical simulations with inputs on muscle forces with personalized attachment and force direction data and outputs of mechanical properties, such as stress, deformation, motion and strain, etc. within bone construct, fragments, fixation means and bone plates. The stress determination step can thus be based on any physical parameters, either measured or deduced from indirect measurements, and subject to ponderation and/or weigh evaluation. Alternatively or in addition, some of the considered parameters may be evaluated without measurement by the surgeon and/or the patient. Preferably, only measured parameters are considered. Alternatively or in addition, some or all of the suitable parameters may be considered by an artificial intelligence algorithm to determine a stress profile.

In one embodiment, optimization may be based on minimizing inter-fragmentary motion. The mechanical behavior of a given bone fragment may be evaluated based on several parameters such as the position of such a bone fragment within the fractured bone 1. An outer position, like in a cortical bone, may be considered as receiving a heavier mechanical load than a central position, like in a cancellous or trabecular bone. The musculoskeletal environment of the bone fragments F1, F2, F3, F4 is also considered. In particular, the point of attachment and force direction of the muscles (through tendons) on the bone fragment F1, F2, F3, F4 may be considered. The bone fragments bearing points of attachment of the muscles may be exposed to a heavier mechanical load than a fragment free of muscles. Other parameters related to the patient morphology may be considered, in particular the body weight, the sex, and/or the age of the patient may impact the mechanical load at the bone fragments F1, F2, F3, F4. The daily activity of the patient before the bone fracture and mainly during the healing phase also impacts the mechanical load at the bone fragments F1, F2, F3, F4. In particular, parameters such as magnitude of overall joint load, muscle load and direction acting on specific fragments may be considered. Other type of stresses may be considered for each bone fragments F1, F2, F3, F4, such as physiological stress. The porosity of the bone 1 may increase the effect of the mechanical load. Also the soft tissues and/or blood supply surrounding the bone fragments F1, F2, F3, F4 may be considered. In particular the integrity of these soft tissues and required blood supply may affect fracture healing. Other patient related factors such as health status, smoking and drinking habits, or other patient related information can be considered in the determination of the stress level. The term "stress level" is thus a parameter resulting from several other parameters, which aims at evaluating the degree of strength of the fixation of a given bone fragment or in regard to the overall construct stability. Each one of the parameters used to determine the stress level at a given bone fragment may have a predetermined preponderance, saying that some parameters may be considered as having stronger impact than others on the stress level. The preponderance of a given parameter on the stress level may further be optimized or adapted according to other parameters, such as the size of the considered bone fragment or a combination of other parameters.

It is well known that a slight relative motion between the bone fragments (micromotion) helps the healing process. It is however considered that such a micromotion depends on the inherent flexibility of the fixations means and plates used in the reconstruction of the bone. The flexibility of the fixation means and plate and any other elements used in the reconstruction of the bone is thus preferably not a parameter involved in the stress determination level step S12. It can be evaluated and addressed in the following arrangement and bone plate shaping steps (S13 and S22). A strong and rigid fixation arrangement determined based on a high level of stress may finally be slightly lightened to allow the useful amount of micromotion helping the healing process. The construct stability is thus quantified, considering the stress level and the suitable micromotion. The construct stability may be optimized so as to allow load bearing as early as possible during the patient recovery, by allowing the adequate micromotion while preserving the relative positioning of the bone fragments. In addition one or several parameters related to the healing rate of the estimated healing rate may be considered to optimize the bone construct stability over the recovery period. Such parameters may comprise the age, the gender, the health status of the patients as well as any other relevant parameters, either physiological or non-physiological.

Based on the 3D imaging of the bone fragments and their optimal relative positioning determined in the preceding steps S10, S11, S12, the present method allows to determine an optimal fixation arrangement in an arrangement step S13.

Such an optimal fixation arrangement comprises some or all the bone fragments F1, F2, F3, F4 virtually placed at their relative optimal position as defined in the positioning step S11, and one or more fixation means 10a, 10b, wherein one or more of the nature, the size, the number, the orientation and the position of the fixation means 10a, 10b is precisely determined. The orientation and the position of a given fixation means 10a, 10b can be determined in 3D space and relative to specific bone fragments and/or the overall bone construct. It may in addition be determined relatively to the other expected fixation means or any other specific areas M1, M4 of the bone. In one embodiment, the fixation means are defined orthogonal (perpendicular) to the fracture lines based on the positioning step S11. This orthogonal alignment of fixation means could be the input (starting point) for the following steps, particularly the arrangement step S13. Such fixation means may be any fixation means used for bone surgery such as screw, nails, bolts, pins, clamps or stitches or any other means adapted to maintain the bone fragments at a determined relative position. The position and the orientation of the fixation means 10a, 10b denote their presence or not on a given bone fragment and when a given bone fragment is determined to be provided with a fixation means 10a, 10b, its precise location and orientation through the given bone fragment or in near proximity. It is also foreseen that one such fixation mean is used to maintain multiple bone fragments at a designated position, relative to each other and/or within the overall bone construct. The number of bone fragments maintained by a given fixation means is also determined.

For one of the arrangement step S13 and the shaping step S22, or both of them, a generative method design may be used. Generative design means that the design of either the screw arrangement or the bone plates are automatically optimized based on required boundary conditions such as forces acting on the construct (e.g. from biomechanical simulations). Therefore, in the arrangement step, this could help optimizing/minimizing the required fixation means. In the shaping step, generative design method allows optimizing material distribution of the bone plate, while considering the defined fixation means (e.g. reducing material where not necessary).

The position and orientation of the fixation means 10a, 10b may be determined based on the number of the bone fragments or their size or their relative position, as determined through the 3D modelling step S10 and the positioning step S11. Other parameters may be considered in the determination of the position and orientation of the fixation means 10a, 10b (e.g. soft tissues, blood supply, etc.). The stress level, including at least the mechanical load and stability of each the bone fragments is considered, based on the output of the stress determination step S12. The position and orientation of the fixation means 10a, 10b is at least determined to maintain the bone fragments at their optimal relative position during the healing period and also considering the patient related characteristics and expected loads of daily life.

The position/orientation of the fixation numbers 10a, 10b may in addition consider some specific areas M1, M4 of the related bone fragments. Specific areas M1, M4 denotes for example areas of muscle connections or soft-tissue connections or fragility areas on the bone fragments. Such areas may denote osteoporosis and/or weak bone structures. Such specific areas M1, M4 are for example less favourable for implanting fixation means 10a, 10b. Alternatively or in addition, these less favorable areas may require more/or stronger fixation means for adequate stabilization. Such additional or stronger fixation means are preferably arranged around these specific areas. Alternatively, some areas M1, M2 may be considered as more favorable as fixation points, due to their stronger resistance. Based on the output of one or more of the 3D modelling step S10, the positioning step S11 and the stress determination step S12, some areas M1, M4 of the bone fragments may be given a parameter representing the acceptability of a fixation means 10a, 10b. The specific areas M1, M4 may be located at the external surface, such as an articular surface, or in the bulk of the bone fragments. The specific areas M1, M2 may also denote where applicable external elements resulting from a previous surgical operation. They may refer to a bone implant, some fixation pins used to temporarily maintain the bone fragments, or any other external elements.

The number of fixation means 10a, 10b may also be determined so as to provide the best fixation with a minimum fixation means. For example, the optimal fixation arrangement provided in the arrangement step S13 may start by default with one fixation means 10a and determine its best position and orientation to maintain all the bone fragments. In case it is determined that one fixation means 10a is not optimal for repairing the fractured bone 1, then a second fixation means 10b may be considered and integrated in the optimal fixation arrangement. Several fixation means 10a, 10b may thus be successively considered according to iterative processes until an optimal number of fixation means 10a, 10b is determined. Such disadvantages may counter-balance the advantage of having a large number of fixation means 10a, 10b and thus allows to determine the optimal number of fixation means 10a, 10b. Alternatively, the iterative process could also start with a large number of fixation means. Such a large number of fixation means may be initially determined by surgeon, engineer, or even automatically by the arrangement step S13 based on number of contacting surfaces between the different bone fragments (e.g. based on the positioning step S12). In this case, the iterative process includes a reduction of fixation means while maintaining overall bone construct stability. Either one of these approaches would consider re-arrangement of the fixation means to achieve an optimal solution. It is further considered that an optimal orientation or position of fewer fixation means may be different compared to an optimal orientation and position with more fixation means.

The nature of the fixation means 10a, 10b may also be determined during the arrangement step S13. The nature of the fixation means includes their type, such as a screw, a bolt, a pin or any other type of fixation means. The nature also considers the material of the fixation means 10a, 10b. Such material may be stainless steel, titanium containing materials or polymer materials or any other materials usable for implants such as magnesium based resorbable materials. The present method may determine that the different fixation means 10a, 10b necessary for the fixation of the bone fragments are of the same nature or on a different nature, considering either their type or their material. A screw may be considered as the most suitable at a given bone fragment while a bolt is recommended at another bone fragment (e.g. connecting two separate bone plates on either side of the bone).

The size (e.g. length and thickness) of each fixation means 10a, 10b may be individually determined according to one or more of the parameters above-considered. The size of the fixation means 10a, 10b may depend on their location, on their number, on their nature, as well as on the stress level of the bone fragments and any other relevant parameter.

The present method thus allows generative design principles to determine one or several of the position, the orientation, the number, the size, and the nature of the fixation means. According to one aspect, the generative design method aims at limiting the number of fixation means while providing the adequate fixation of the bone fragments. According to another aspect, the generative design method aims at improving the healing rate, for example by allowing adequate micromotion. It is understood that all the parameters and limitations above-mentioned, such as the location of some specific areas M1, M2 are considered for generating an optimal design. The present method provides in addition sufficient flexibility to consider any extra limitations or constraints. For example, the position, the orientation, the nature, and/or the size of a given fixation means may be predetermined as a fixed parameter. The generative design method thus allows to adapt the surrounding fixation means accordingly. For example, it can be predetermined that a specific screw is provided at a specific orientation between two identified bone fragments, for accessibility reason or any other reason. The generative design method thus allows to input such a constraint and optimize the overall arrangement accordingly. In other words, one or more parameter selected from the position, the orientation, the number, the size, and the nature of a given fixation means may be predetermined. This can happen even though such parameter would not have been considered as optimal after computing all the parameter. In that case, the global arrangement is computed so as to remain as optimal as possible. The generative design method may in addition provide an alert in case such a constraint is judged not acceptable, due for example to a significant risk of failure, or a degraded healing quality.

The stress determination steps S12 and the arrangement S13 may be iterated once or several times. In particular, once the position and orientation of the fixation means 10a, 10b is determined in the arrangement step S13, then the stress level of the bone fragments may be computed once more, considering the effect of the fixation means 10a, 10b. It may be determined that the global arrangement provides a stress level on one or more bone fragments (or fixation means) which is not acceptable. It results that one or more of the positions of the fixation means 10a, 10b, their spatial orientation (3D), their nature or their number is automatically revised and optimized. The obtained arrangement may still be open to modification and further iterations. For example, in case a fixation means is considered by the surgeon as not adequate for the practice, it can be manually modified or changed. The overall arrangement is computed so as to be optimized accordingly.

Based on the preceding 3D modelling step S10, positioning step S11, stress determination step S12 and arrangement step S13 a virtual optimal arrangement is determined. This arrangement may also ensure fixation means do not interfere with each other, or with other permanent or temporary structures such as tools, guides or reference geometries. Such a virtual arrangement corresponds to the arrangement targeted by the surgical operation. Examples of such final arrangement are schematically shown in FIGS. 2, 3, 4, 5, 7 and 8. This final arrangement may be provided to the surgeon or an engineer or any other suitable person, on any suitable support. It may for example be supplied as a numerical file allowing the 3D visualisation on a screen or through virtual reality device, or through augmented reality device or any other adapted device. Alternatively or in addition, the final arrangement may produced as a 3D printed model, wherein all or some of the elements can be separated from each other to allow the surgeon clearly visualise all the details. It is here understood that the final arrangement is materialized by any suitable means.

In addition to the spatial arrangement of the bone fragments and the fixation means 10a, 10b, the present method comprises an ordering step S14 of determining chronological order of placing the fixation means 10a, 10b during the operation (e.g. personalized surgical technique, plan, etc.). For example, it may be determined that a given fixation means 10a should be placed first on the related bone fragment. Several parameters may be considered such as the stress level of the bone fragments, the ease of placing the fixation means 10a, the effect of the fixation means 10a regarding the stability of the bone fragments. In addition, a range of importance of each fixation means may be determined, including planned and unplanned fixation means. The ordering step S14 may also consider the relative importance of these fixations means. The arrangement and ordering steps S13 and S14 may particularly be affected by pre-existing implants such as hip or knee arthroplasty, or other hardware present in the bone of a given patient. Particularly, characteristics such as position, orientation, length and ordering, of fixation means may be determined according to the existing implant and any other specific areas M1, M2 of the bone. Preferably, the fixation means are not allowed to touch, interact, interfere, with the potential existing implants. See in particular FIG. 8. The arrangement may further result in solutions where two or more bone fragments are first screwed together separately and then placed in the overall construct, as shown in FIG. 7. In such a configuration, screws may be located fully within the bone construct without being accessible through the outside cortex. The ordering step S14 thus allows to determine sub-constructs. Depending on the situation, the material may be specified or suggested in the planning. In this case it may be beneficial to use materials that will eventually self-resorb within the bone (e.g. bioresorbable materials such as magnesium based screws, etc.). Although an optimized ordering is automatically generated, the surgeon may input a specific ordering or some personalized surgical technique or plan. The ordering may thus be subject to a further computing step aiming at evaluating such an imposed ordering. Following this computing step, the global ordering may be further optimized and/or an alert may be provided if the imposed ordering is considered risky.

The present method may further comprise a step S2 of determining the shape of one or more bone plates 11, as shown in FIGS. 3, 4, 5, 7, 8 based on the output of the steps S10, S11, S12, S13 and S14. In particular, the step S2 comprises the step S21 of determining whether a bone plate 11 is necessary or not. For example, when it is determined in step S1 that the resulting virtual optimal arrangement does not provide enough cohesion strength to maintain the bone fragment in their optimal relative position during the healing period, then it is considered that a bone plate 11 should be added. Otherwise, it is considered that a bone plate 11 would not be necessary considering either the cost, the time of the operation, the physiological risks, such as response of the body to implanted hardware (e.g. minimize hardware) or any other relevant parameters.

The step S2 of the present method comprises a shaping step S22 of determining the shape of the bone plate 11, if it was considered necessary in step S21. The shape of the bone plate 11 is determined based on the 3D model of the bone fragments, and in particular the global shape of the optimal arrangement, including the fixation means, determined through the steps S10, S11, S12 and S13. The external surface of the bone fragments, and mainly the combined surface of the assembly of the bone fragments and optimized arrangement of the fixation means may be considered to determine the shape of the bone plate 11. The shape of the bone plate 11 may thus be defined so as to correspond to the external shape of the bone in the optimal arrangement. Further, the shaping step may also account for mechanical properties of the bone plates, similar to the stress determining step S12 for fixation means. Hence, the size, shape, position, etc. may be optimized based on simulated mechanical parameters (load, stress, strain, deformation, etc.), which may be based on the described generative design method and topology optimization. Alternatively, the shape of the bone plate may also be defined to achieve reduced local contact to the bone surface, thus limiting pressure on the periosteum. In addition, the shape of the bone plate 11 is determined according to the size, position and orientation of the fixation means 10*a*, 10*b*. Depending on the stress level determined in the stress determination step S12, or other parameters such as the surrounding of the bone, the thickness of the bone plate 11 may be locally adapted (illustrated in FIGS. 6*c* and 6*d*). The shape of the plate 11 may also consider the pre-existing fixation means such as pins or temporarily fixation means. The shape of the plate may also consider simulated parameters such as the expected overall construct stability. For example, in case it is determined that a given bone fragment receives a high mechanical load, then the bone plate 11 may be thicker at the vicinity of such a bone fragment. Alternatively or in addition, the bone plate 11 may be locally larger. Global shape of the bone plate 11 may include some holes or recesses corresponding to the fixation means 10*a*, 10*b*. The dimensions of the bone plate 11 may also be adapted to the size of the bone 1, eventually considering the specific areas M1, M4. It may be considered that the bone plate 11 should not overlap with some or all of the specific areas M1, M4. The shape and the positioning of the bone plate 11 thus depend on several parameters determined in the preceding steps, and in particular on the position and orientation of the fixation means 10*a*, 10*b*. Additionally, physiological factors such as blood supply required for healing, or interaction with soft tissues such as tendons, ligaments or nerves, may be considered for the shaping of the bone plate. In particular, it can be determined that the plate location might require absence of plate material, increased distance, etc. based on soft-tissue constraints. This could be determined automatically by an algorithm (e.g. use of artificial intelligence (deep learning) or by engineers, doctors (surgeons)). The shaping step S22 include the determination of the number of necessary plates 11 in addition to their specific shape. It may be determined that two smaller bone plates are preferable compared to one larger bone plate or the other way round for a given situation. FIGS. 3, 4, 5, 7 and 8 show examples of such plates 11 implementation. The shaping step S22 may consider where applicable pre-existing elements such as previous implant, pins, temporarily fixation means, previous bone plates resulting from an antecedent operation, whether they remain in place or are intended to be removed or replaced. The size of bone plates may be reduced, in particular to limit the contact surface with the bone fragment. A bone plate preferably comprises or is combined with at least one fixation means such as a screw). A bone plate being associated to one fixation means essentially represents a washer with an interface to the fixation mean, including specific direction and/or orientation of the fixation means with regard to the plate. It is furthermore considered as a specifically designed interface to the respective bone surface. It may result that one large bone plate with additional single fixation means is the most beneficial result, considering overall construct stability to be achieved through minimal hardware. The shaping step S22 may thus include the determination of the suitable number of fixation means associated to a given plate 11, said number being 1, 2 or more than 2. The shaping step S22 thus allows to provide the shape and the number of bone plates 11 necessary for a given operation. It also allows to supply these data to the surgeon, an engineer or a producer of bone plates, on any suitable support. The resulting bone plate shape and number can be for example provided as a numerical file, readable on a computer on various view or by the means of virtual reality device. Alternatively or in addition, specific indications such as dimensions, material, thickness, length, width, position and orientation of potential holes, including angles, may be included in the file. For example, FIGS. 6*a* and 6*b* show a similar bone plate shape/design with different interface orientations for intended fixation means that are tailored to a specific fracture pattern. In a simplified version of the shaping step standardized bone plate may already be pre-designed (e.g. various designs, sizes, etc.), in which case the shaping step is used for determining size and type of such pre-designed bone plates. The bone plate as such visualized may be isolated from the final bone construct, as provided after the arrangement step S13. The shaping step S22 may result to a digital file allowing its manufacturing.

Once the shape of a bone plate 11 is determined in the shaping step S22, then a production step S23 may be initiated to produce the bone plate 11. Depending on the used material of the bone plate 11, its production may be done through additive manufacturing operations, machining operations, moulding operation or any other common manufacturing operations as well as combination thereof. The production step thus uses the numerical values obtained in the previous shaping step S22.

Based on the output of the first step S1, wherein at least the position and the orientation of the fixation means 10*a*, 10*b* are determined, and eventually the output of the second step S2, it may be initiated a third step S3 of designing one or more instruments to place the bone fragments and the fixation means 10*a*, 10*b* according to the optimal arrangement as determined in the arrangement step S13. Instruments includes any element in addition to the fixations means 10*a*, 10*b*, and the bone plate 11, which are used during or for the operation. They include the potential specific tools T1, T2 such as clamps adaptors designed to maintain some bone fragments at a given position. FIG. 9 shows an example of such a tool T1, T2. The instruments also designates any specific guides which are necessary to properly orient and place the fixation means 10*a*, 10*b* and/or the bone plates 11. Specific surgical tools may include patient specific attachments to standard clamps (in one embodiment the end of the standard clamp provides a connection to a piece with an interface matching a specific area of the bone (or bone fragment) for each side of to clamp. This would serve as a reduction (positioning) aid to ensure the bone fragments are pushed together in a specific way based on the positioning step S11 and the arrangement step S13. There may be specific interfaces of these patient specific attachment pieces to the patient specific plates or guides and bring them into position directly through the clamp or have an interface to pins (e.g. k-wires), drills, screws, etc. for appropriate implementation of the fixation means (or preliminary fixation aid such as a pin), according to the arrangement step S13. The interface of these reduction aids may go directly to a specific area of the bone or alternatively the skin or any other reference point, such as pins. These pins may be added at specific areas of the bone and possibly be represented (added) in the virtual 3D model, either through intraoperative measures (e.g. surface matching, digitization or imaging) or based on preoperative imaging (e.g. CT, x-ray, etc.). If preoperative external fixation (e.g. preliminary fixation of one or more bone fragments) is performed before a CT scan is taken, these reference points (e.g. pins or other geometries) could be added to the virtual 3D model from the beginning and used as a reference for tools (e.g. reduction aids) and guides (e.g. drill guides for implementing positioning means) based on desired bone alignment determined in the positioning step S13). The reference points could also be used to achieve proper length and rotation of the overall bone reconstruction as determined in the positioning step (e.g. also include simpler fracture patterns but with a difficult/minimal anatomical references for bone alignment such as circular and concave geometries). These references could also be used for an accurate final optimal positioning of the bone plate. This could be used for the proposed patient specific implant or in other cases for positioning standardized implants, when the proposed process is applied to standardized implants, with obvious limitations in regards to spatial positioning of the fixation means and limited plate design (e.g. limited pre-defined designs and different sizes). In this case, the rest of the process could still be used for optimized selection and positioning of the plate to the bone (e.g. standard plate used with patients specific instruments for optimized positioning based on personalized planning) as well as choice of pre-determined fixation possibilities and limited orientation thereof for a given position on the plate (e.g. predefined screw hole). In any of the above-mentioned applications, the reference info could also be transferred to a virtual reality system (e.g. augmented or mixed reality) or physical models such as additively manufactured models, allowing the surgeon to see references in the actual and desired configuration. This could be particularly useful during the positioning step S11 and the implementation of the arrangement step (e.g. relative positions of different bone fragments to each other or instrument (or implant) positioning relative to one or more bone fragments.

The step S3 comprises a step S31 of determining whether an instrument is necessary or not. The step S3 further comprises the instrument-designing step S32 wherein the shape and the nature of the instrument are defined. Such an instrument may be for example a specific clamp to maintain the bone fragments assembly while proceeding to the fixation operation. The bone fragments must indeed remain at their optimal relative position, as virtually defined in the optimal arrangement defined in the arrangement step S13. The instrument can be alternatively a guide helping orienting the fixation means 10a, 10b according to the optimal arrangement, as illustrated in FIGS. 6a, 6b. Such guides allow to drill the fixation means at predetermined angles x1, x2, β1, β2, resulting in the corresponding reconstructed bone shown in FIGS. 6c and 6d. Any other specific instruments may be designed according to the specificities of the situation. The step S3 further comprises the tool production step S33 of producing the instruments. Depending on the shape and the material of the tool, its production may be done through additive manufacturing operations, machining operations, moulding operation or any other common manufacturing operations as well as combination thereof.

It results from the first step S1 the second step S2 and, where applicable, the third step S3 sequence a preoperative planning usable by the surgeon. The present method thus comprises a fourth step S4 of providing a preoperative planning. Such a preoperative planning may also designate a systematic plan. In case a bone plate 11, and/or one or more instruments are necessary, then the corresponding bone plates 11, instruments, are produced and delivered to the surgeon together with the necessary fixation means 10a, 10b. A kit may be prepared, comprising all the necessary fixation means 10a, 10b, the bone plate 11 and the tools when necessary, and a preoperative planning including one or more of the 3D model of the optimal arrangement, the 3D model of each bone fragments, the order of the fixation means placement. The fixation means 10a, 10b, the bone plate 11 and the instruments, if present, may be delivered under sterile packages or may be object of a sterilisation step before the operation.

The preoperative planning may be delivered to the surgeon as a numerical file showing at least the 3D virtual optimal arrangement elaborated in the arrangement step S13. The numerical file may be stored on any known storage device such as a USB key, a hard disc, or any equivalent storage device. Alternatively, the preoperative planning may be delivered to the surgeon through a link to a remote server, having a secured access or not. Then, the preoperative planning may be visualized on a screen, either a computer screen or a 3D visualisation device such as 3D glasses, virtual reality headset, an augmented reality device, or any equivalent visualisation device. The preoperative planning may in addition comprise a dynamic animation showing the order of placement of the fixation means 10a, 10b, and the bone plate 11 if present and/or the tools, if present. Such a dynamic animation thus allows to visualize the chronological steps of the surgery to be practiced. Alternatively, the preoperative planning may comprise indications, such as written indications related to the ordering and chronological steps. The preoperative planning may in addition be interactive, saying that user or the surgeon, when visualizing it, can decide on the angle of view, the number of elements shown, the colours, or any other visualisation parameters. In an alternative variation, steps S1-S3 could be set up with real-time (or certain delayed-time) update during the surgery. In this case certain constrains may apply but actual surgical application such as specific intra-operative alteration of the predefined surgical plan could be updated. For multi stage surgical procedures, the first stage surgery could be used as an input for the steps S1-S2 described above. Some of the constraints may also depend on the urgency and time lapse between the surgical stages, such as possible additional manufacturing requirements. For example a part could be delivered or possibly manufactured at the hospital through 3D printing at point of care. Either actual instruments or implants could be printed at the point of care. Alternatively, physical models for non-surgical use could be printed even in the doctors office. These models could even better visualize preoperative planning and possibly highlight key steps of the planned procedure (e.g. most critical steps shown as "before and after"3D printed models. Such models could further serve for discussions of the case and plan with patients, colleagues, etc. Such models may in addition be used for educational purpose and be shared with students.

The preoperative planning may be implemented in a virtual reality or an augmented reality program. It may be for example used as a training program or participate to a training program of the surgeons.

The preoperative planning, as well as the data used to elaborate it, may in addition or alternatively feed a database related to bone fixation operations. Such a database may be used in combination with an artificial intelligence software to better elaborate preoperative planning related to the bone surgery.

All of the above step sequence may be fully automated based on the 3D models generated in the 3D modelling step S10 and additional input values such as patient related information or other parameters. The patient related parameters such as age, gender, daily activity, health status, smoking or drinking habits, etc. may be object to a set of numerical values usable in the computation for generating the bone fixation preoperative planning. The geometrical parameters of the bone fragments, including their number and relative position may be object to another set of numerical values, which are generated based on the 3D model. Additional parameters such as the stress level, including the mechanical load on each of the bone fragments, their potential specific areas M1, M2, and any other parameters regarding the environment of the fractured bone 1 may be object of another set of parameters, either generated based on the above-mentioned sets of parameters or directly implemented in the computing process. All of these parameters or a part of these parameters may be combined and computed through a specific algorithm, including some predetermined precedence and weight.

It may be possible that a user of the method or the surgeon himself can modulate the relative importance of a given parameter in the computing process. For example, the constraint related to the mechanical stress on some bone fragments may be voluntary minimized or maximized by the user. Alternatively or in addition, some specific constraints such as the presence of specific areas M1, M4 may arise and be manually implemented in the computing process. Some surgeon preferences may also be considered for tuning the computing process. The resulting preoperative planning can thus be modified according to the human change in the way of computing the parameters of the method.

At any step during this process there could be approval steps by the engineer, surgeon, hospital, manufacturing facility, or any other referent person. For example before the production steps S23 and S33 the surgeon provides approval of implants, instruments and associated preoperative planning (surgical plan). Some of these parameters such as surgeon preferences may further be stored in a data base for future predictions of the desired strategy for a given surgeon (e.g. through manual imputes or automatic predictions using artificial intelligence/deep learning based on specific surgeon's (or hospital) previous cases.

In the disclosed method, any main steps S1, S2, S3, and S4 may be independently performed depending on the needs. The present method may be for example focused on the design of the bone plates and the instruments necessary to the operation. The result of each individual steps S1, S2, S3, and S4 may be addressed to distinct persons, such as a manufacturer, an engineer, a surgeon, a medical doctor or any suitable person.

The present method may comprise a fifth step S5 of postoperative follow up. The fifth step S5 may for example comprise one or more evaluation steps S51 based on 3D imaging allowing to determine the relative position of the bone fragments, the fixation means 10a, 10b, and the bone plate 11 if present, during the healing period. The fifth step S5 can thus comprise an optimisation step S52 to determine whether the bone fragments are actually positioned according to the optimal arrangement determined in the arrangement step S13 or not. In case of deviation compared to the arrangement determined for the preoperative planning, some additional parameters may be integrated in the modelling process, so as to further optimize the computing process. Such additional parameters may be some additional patient related information, such as his/her daily activity or specific event. The precedence or weight of some parameters used in the first step S1 or in the second S2 and third S3 steps may thus be optimised. Postoperative follow up may also be useful to quantify the construct stability of a given patient, during specific daily activities and define the allowed level of activities during rehabilitation. Without any quantification it is common to immobilize patients for 8-12 weeks following surgery, which is mainly due to the unknown construct stability. The present method allows to better know the construct stability. It results that patients may be allowed for early weight bearing. For example, patients may start weight bearing within 6 weeks of surgery, preferably withing 4 weeks or even two weeks, instead of 8 to 12 weeks.

Post-operative evaluation may particularly be relevant for revision surgeries where the bone reconstruction has failed. If the healing process fails to combine some bone fragments, the reason for failure could be evaluated and additional requirements could be determined such as initial preoperative imaging for bone reconstruction and the data of the failed procedure. Therefore, this optimization process provides particular benefits for revision surgeries, considering the initial treatment (either following this process or using state of the art methods) did not provide sufficient stability and choices might be more limited due to unfavourable physiological and/or mechanical conditions). This process provides particular benefits for such failed treatments considering the importance and difficulties of a revision surgery. Failure reasons of the initial bone reconstruction may be identified by the present method. Appropriate new measures can be taken to plan for sufficient bone stability with revision surgery thanks to the present method.

The expression "relative position", when referring to the bone fragments, designates the position and the orientation (e.g. spatial arrangement in 3D including rotations, translations and positions in space or on surfaces) of the bone fragments relative to the other bone fragments. It may further refer to tools, guides, fixation means, implants, etc. relative to one another or relative to one or more bone fragments or other reference points/geometries described above.

The expression reduction (also anatomical reduction) refers to the medical term for realignment, positioning, reconstruction of individual bone fragments relative to each other and relative to the native anatomical shape. This is intended during the positioning step S11.

The expression articular surface refers to the area of the bone that is articulating with another bone and generally coated with a low friction cartilage surface (for motion/articulation with other bones). This area is generally located at the end of long bones and the location of load transfer to adjacent bones.

The expression periarticular means through the articulation (or through the joint) and refers to fractures that going into a joint (e.g. through the articular surface of a given bone).

The expression biomechanical simulation refers to any type of simulation that includes mechanical and/or biological information and includes various simulation methods (e.g. Finite Element Analysis (FEA), rigid body simulations, musculoskeletal simulations (e.g. muscles are represented through forces and ligaments through springs, both directed in three dimensional space (e.g. position/location coordinates and directional coordinates). It could further refer to modelling of soft tissues given various parameters.

The expression fixation mean includes any type of fixation that may or may not remain inside the patient permanently. Fixation means include but are not limited to screws, nails, bolts, pins, rods, staples, clamps etc. This includes standard materials such as titanium or stainless steel but may also include polymers and resorbable materials such as magnesium or biological materials.

The expression instrument incudes any tool, guide or other equipment used during surgery that does not remain inside the patient. Instruments include but are not limited to drill guides, clamps, spacers, blocks pliers, holders, pins, trial implants, etc. Instruments can be specifically tailored to patient's anatomy and fracture patterns for easier use during the surgery when compared to standard instruments. There may also be a combination of standard and patient specific instruments (PSI).

REFERENCE SYMBOLS IN THE FIGURES

S1 First step
S10 3D modelling step
S11 Positioning step
S12 Stress determination step
S13 Arrangement step
S14 Ordering step
S2 Second step
S22 Shaping step
S23 Production step
S3 Third step
S32 Tool designing step
S33 Tool production step
S4 Fourth step
S5 Fifth step
S51 Evaluation step (3D imaging)
S52 Optimisation step
F1, F2, F3, F4 Bone fragments
F10, F20, F30, F40 Surfaces of the bone fragments
M1, M4 Specific bone areas
1 Fractured bone
10a, 10b Fixation means
11 Bone plate
12 Temporary external fixation means
13 Drill guide

The invention claimed is:

1. A computed-implemented method for generating a bone fixation preoperative planning for repairing a fractured bone comprising several individual bone fragments by means of one or more fixation means, the method comprising:
a first step comprising a 3D modelling step; providing using a computer, a 3D model of each of the individual bone fragments of the fractured bone, and
a positioning step; determining using the computer, the best relative position of these bone fragments, based at least on their respective surfaces and interfaces,
wherein said first step further comprises a stress determination step using biochemical simulations, including musculoskeletal modelling, and finite element analysis (FEA), by the computer, based on parameters including the von Mises stress, principal stress, strain, deformation, displacement and reaction forces, so as to determine stresses applied to each of these bone fragments and the fixation means, including mechanical load and physiological stress, and
an arrangement step providing using the computer, at least one virtual arrangement of the individual bone fragments and the fixation means,
so that one or more of the nature, the size, the number, the orientation, the position of the fixation means, and the preferred order of placement of the fixation means is determined for an optimal healing process.

2. The computer-implemented method according to claim 1, wherein said stress determination step further determines an optimal micromotion adapted for improving the healing process.

3. The computer-implemented method according to claim 1, wherein the arrangement step is based on one or more of a stress level determined in the stress determination step and a free space between the bone fragments.

4. The computer-implemented method according to claim 3, wherein
the stress determination step and the ordering step are iterated one or several times, to further determining the stresses resulting from the fixation means, and provide an optimized ordering of the fixation means.

5. The computer-implemented method according to claim 1, wherein the step further comprises an ordering step; determining at least one order of placement of the fixation means.

6. The computer-implemented method according to claim 1, wherein
the stress determination step and the arrangement step are iterated one or several times, in order to further determining the stresses resulting from the fixation means, so as to further optimize fixation means.

7. The computer-implemented method according to claim 1, further comprising a second step of defining a shape of one or more bone plates, based on an output of the first step, wherein the optional second step comprises:
a step of determining whether a bone plate is necessary,
a shaping step of determining the shape of the bone plate if considered necessary,
a production step of producing the bone plate,
wherein the shaping of the bone plate is based on results of the arrangement step, including already present element resulting from previous operations, and/or physiological factors.

8. The computer-implemented method according to claim 7, wherein the shaping of the bone plate includes the determination of an optimal number of bone plates.

9. The computer-implemented method according to claim 1 further comprising a third step, comprising
a step of determining whether one or more instruments are necessary,
an instrument designing step of designing the instruments to be used, and
an instrument production step of producing the instruments wherein said instrument denotes any tools or guide necessary for the realisation of the preoperative planning, such as pins, rods, other geometric shapes.

10. The computer-implemented method according to claim 9, wherein the instrument designing step consider reference geometries of any bone and non-bone elements already present during the first step, such as bone pins of external fixation.

11. The computer-implemented method according to claim 1, wherein said bone fixation preoperative planning is provided as a numerical file or a 3D printed object, wherein several or all of the elements can be separated and individually visualized.

12. The computer-implemented method according to claim 11, wherein one or several parameters selected from the nature, the size, the number, the orientation, and the position of a given fixation means can be predetermined, and wherein the nature, the size, the number, the orientation, and the position of the other fixation means are automatically optimized.

13. The computer-implemented method according to claim 1, further comprising a postoperative step comprising
- an evaluation step through 3D imaging of imaging the bone fragments arrangement after the fixation operation, and
  - an optimisation step of comparing the arrangement as visualized in the 3D imaging step with the virtual arrangement determined in the arrangement step and identify potential deviations, and correcting or modifying one or more of the parameters used in the first step.

14. The computer-implemented method according to claim 1, wherein at least the first step is executed through algorithms which are computer implemented, based on the 3D modelling of the bone fragments obtained in the 3D modelling step, wherein one or more parameters selected from the position, the orientation, the number, the size and the nature of a given fixation means may be predetermined or manually modified.

15. The computer-implemented method according to claim 1, wherein the stress determining step and/or arrangement step are executed through algorithms which are computer implemented, so as to automatically determine one or more of the nature, the size, the number, the orientation, and the position of the fixation means.

16. A preoperative planning elaborated according to the method of claim 1, comprising a numerical file comprising at least the 3D virtual arrangement elaborated in the first step, and optionally a bone plate, instruments and/or tool,
  wherein the preoperative planning is stored in a numerical storage device like a USB key or stored in a server and delivered to the surgeon through a web link, or a web interface, either free or secured, so as to be visualized on a computer screen or through virtual reality device or through an augmented reality device and/or said bone plate, instrument and/or tools can be produced.

* * * * *